United States Patent
Hoy, IV et al.

(10) Patent No.: US 10,294,190 B2
(45) Date of Patent: May 21, 2019

(54) REDUCED FOULING PROCESS FOR THE PRODUCTION OF METHYL METHACRYLATE

(71) Applicant: Rohm and Haas Company, Philadelphia, PA (US)

(72) Inventors: Stacy W. Hoy, IV, Houston, TX (US); Joy L. Mendoza, Seabrook, TX (US); Mingyu Ye, Deer Park, TX (US); Philippe P. Maillot, Kingwood, TX (US)

(73) Assignee: Rohm and Haas Company, Philadelphia, PA (US)

( * ) Notice: Subject to any disclaimer, the term of this patent is extended or adjusted under 35 U.S.C. 154(b) by 0 days.

(21) Appl. No.: 15/521,421

(22) PCT Filed: Oct. 13, 2015

(86) PCT No.: PCT/US2015/055211
§ 371 (c)(1),
(2) Date: Apr. 24, 2017

(87) PCT Pub. No.: WO2016/069252
PCT Pub. Date: May 6, 2016

(65) Prior Publication Data
US 2017/0298000 A1    Oct. 19, 2017

Related U.S. Application Data

(60) Provisional application No. 62/068,996, filed on Oct. 27, 2014.

(51) Int. Cl.
| C07C 67/20 | (2006.01) |
| C07C 67/58 | (2006.01) |
| B01D 3/42 | (2006.01) |
| B01J 19/18 | (2006.01) |
| C07C 69/54 | (2006.01) |

(52) U.S. Cl.
CPC ............ *C07C 67/20* (2013.01); *B01D 3/4294* (2013.01); *B01J 19/1875* (2013.01); *C07C 67/58* (2013.01); *C07C 69/54* (2013.01); *B01J 2219/0004* (2013.01)

(58) Field of Classification Search
CPC ......... C07C 69/54; C07C 67/20; C07C 67/58; B01D 3/4294; B01J 19/1875; B01J 2219/0004
See application file for complete search history.

(56) References Cited

U.S. PATENT DOCUMENTS

| 2,472,487 | A | 6/1949 | Lovell |
| 3,006,950 | A | 10/1961 | Francis et al. |
| 3,210,419 | A | 10/1965 | McConnell et al. |
| 3,821,286 | A | 6/1974 | Pai et al. |
| 5,403,963 | A | 4/1995 | Adamski et al. |
| 6,545,176 | B1 | 4/2003 | Tsay et al. |
| 7,253,307 | B1 | 8/2007 | Carlson, Jr. et al. |
| 2002/0188153 | A1 * | 12/2002 | Tsay .................. B01J 19/02 560/215 |
| 2010/0069662 | A1 | 3/2010 | Gropp et al. |
| 2014/0051886 | A1 | 2/2014 | Broell et al. |

FOREIGN PATENT DOCUMENTS

| CN | 1550489 | * | 12/2004 |
| CN | 1304357 | C | 3/2007 |
| EP | 0561264 | * | 9/1993 |
| EP | 0561264 | A2 | 9/1993 |
| EP | 0686623 | A1 | 12/1995 |
| EP | 0999200 | A1 | 5/2000 |

OTHER PUBLICATIONS

CN1550489 Translation (Year: 2004).*

* cited by examiner

*Primary Examiner* — Yevgeny Valenrod
*Assistant Examiner* — Blaine G Doletski
(74) *Attorney, Agent, or Firm* — Brian L. Mutschler

(57) ABSTRACT

Fouling of an MMA process is reduced by strategically removing an aqueous slip stream.

6 Claims, 1 Drawing Sheet

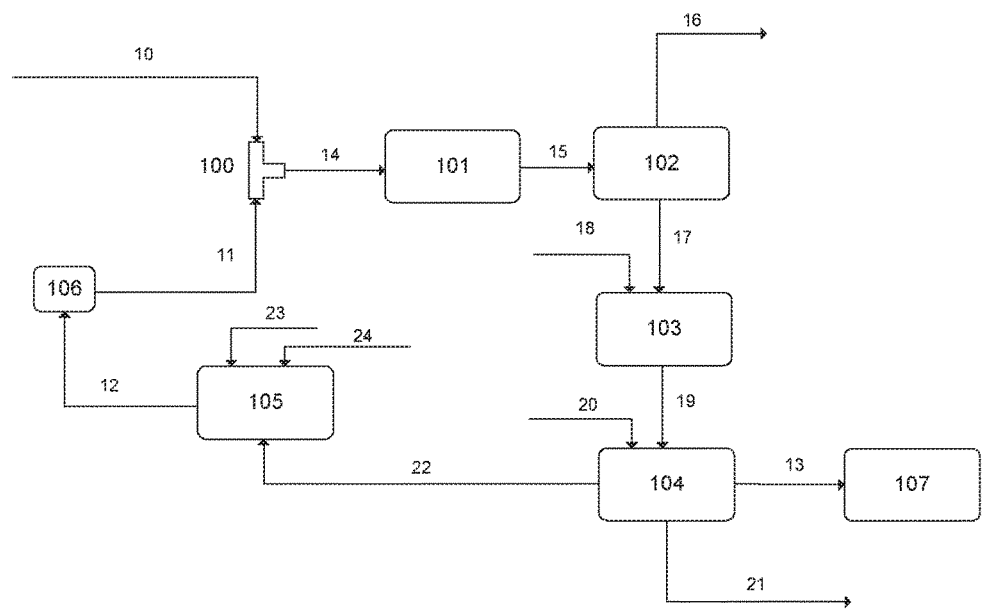

REDUCED FOULING PROCESS FOR THE PRODUCTION OF METHYL METHACRYLATE

BACKGROUND OF THE INVENTION

The invention relates to a process for producing methyl methacrylate (MMA).

MMA is a widely-produced industrial chemical that readily polymerizes. Typical end-use applications include: acrylic plastic sheeting; molding resins; polyvinyl chloride modifiers; processing aids; acrylic lacquers; floor polishes; sealants; auto transmission fluids; crankcase oil modifiers; automotive coatings; ion exchange resins; cement modifiers; water treatment polymers; electronic adhesives; metal coatings; and acrylic fibers. Methacrylate esters are especially prized in these applications and others because of the hardness they impart to the products in which they are used. The most popular industrial process for making MMA is the acetone cyanohydrin ("ACH") process. Methacrylate ester plants produce extremely large volumes of product; thus, any improvement in process yield, however slight, can have a significant positive economic impact.

In a conventional ACH process for the production of MMA, ACH is hydrolyzed in the presence of sulfuric acid to produce α-hydroxyisobutyramide ("HIBAM") and α-sulfatoisobutyramide ("SIBAM"). Next, the HIBAM and SIBAM are cracked to form methacrylamide (MAM) and by-products. The MAM is then esterified with methanol to produce the desired MMA product. The esterification product stream is a mixed product that is subjected to separation and purification steps to isolate the MMA product from the other compounds. Typically, a purified MMA product stream is produced, along with a purification residue comprising other compounds.

U.S. Pat. No. 7,253,307 prescribes the use of polymerization inhibitors to minimize polymer formation in a methyl methacrylate/methacrylic acid production process. The exhaustive list of inhibitors includes phenothiazine and its derivatives, hydroquinone and its derivatives, alkoxy-phenols, nitrosophenol and its salts, copper salts, and radical traps such as 4-hydroxy-2,2,6,6-tetramethyl-piperidinyloxy. The process relies on free-radical inhibitors present in the feed streams to the esterification reactor to prevent polymer formation in the reactor. These inhibitors are designed primarily to limit the concentration of free radicals and free radical polymerization, which leads to equipment fouling. However, despite the use of polymerization inhibitors, commercial MMA plants continue to face significant fouling issues.

In view of the shortcomings of the prior art, it would be desirable to have an improved process that would reduce unwanted formation and/or accumulation of undesired polymer in the production of MMA.

SUMMARY OF THE INVENTION

The process of the invention is such a process, comprising (a) feeding to a phase separation zone an aqueous composition comprising components of varying water solubility; (b) allowing the components to phase separate into a primarily aqueous layer and a primarily organic layer, the layers having a common interface; (c) taking a slip stream from the zone at or below the height of the interface in order to remove soluble and/or insoluble polymer from the phase separation zone.

In one embodiment of the invention, the process comprises: (a) contacting MAM with methanol in an aqueous reaction medium in an esterification reaction zone in the presence of an acidic raw material to produce a first stream comprising MMA, water, methanol, acidic raw material and MAA; (b) phase separating the first stream in a first phase separating apparatus into a first aqueous phase comprising the acidic raw material, and a first organic liquid product phase comprising MMA, methanol and MAA; (c) taking a first organic stream from the first organic liquid product phase, and neutralizing the MAA of the first organic stream with ammonia to produce a neutralized stream comprising MMA, methanol and ammonium methacrylate; (d) optionally adding water to the neutralized stream; (e) phase separating the neutralized stream in a second phase separating apparatus into an organic layer comprising MMA and an aqueous layer comprising methanol and ammonium methacrylate, the layers having a common interface; and (f) removing a polymer-removing stream from the phase separating apparatus at or below the height of the interface.

Surprisingly, the process of the invention removes accumulated polymer from the underlying chemical production process, and also reduces the rate of polymer formation. This allows longer production process run times, and reduces process downtime related to polymer removal.

BRIEF DESCRIPTION OF THE DRAWINGS

The FIG. is a process flow diagram showing a process comprising one embodiment of the invention.

DETAILED DESCRIPTION OF THE INVENTION

As used herein, "a," "an," "the," "at least one," and "one or more" are used interchangeably. The terms "comprises," "includes," and variations thereof do not have a limiting meaning where these terms appear in the description and claims. Thus, for example, an aqueous composition that includes particles of "a" hydrophobic polymer can be interpreted to mean that the composition includes particles of "one or more" hydrophobic polymers.

Also herein, the recitations of numerical ranges by endpoints include all numbers subsumed in that range (e.g., 1 to 5 includes 1, 1.5, 2, 2.75, 3, 3.80, 4, 5, etc.). For the purposes of the invention, it is to be understood, consistent with what one of ordinary skill in the art would understand, that a numerical range is intended to include and support all possible subranges that are included in that range. For example, the range from 1 to 100 is intended to convey from 1.01 to 100, from 1 to 99.99, from 1.01 to 99.99, from 40 to 60, from 1 to 55, etc.

Also herein, the recitations of numerical ranges and/or numerical values, including such recitations in the claims, can be read to include the term "about." In such instances the term "about" refers to numerical ranges and/or numerical values that are substantially the same as those recited herein.

Unless stated to the contrary, or implicit from the context, all parts and percentages are based on weight and all test methods are current as of the filing date of this application. For purposes of United States patent practice, the contents of any referenced patent, patent application or publication are incorporated by reference in their entirety (or its equivalent U.S. version is so incorporated by reference) especially with respect to the disclosure of definitions (to the extent not inconsistent with any definitions specifically provided in this disclosure) and general knowledge in the art.

As used herein, the terms "decanter," "phase separator," "phase separating apparatus," "phase separation zone" and "phase separation vessel" are interchangeable, and refer to an apparatus, vessel, or device in which an input stream is allowed to separate into at least 2 phases, such as a primarily organic phase and a primarily aqueous phase.

The ACH process for the preparation of MMA comprises: (i) continuously feeding a first raw material comprising acetone cyanohydrin and an acidic raw material into a hydrolysis system; (ii) continuously hydrolyzing said first raw material in said hydrolysis system to form a hydrolysis product comprising SIBAM and HIBAM; (iii) continuously feeding said hydrolysis product to a cracking system; (iv) continuously cracking said hydrolysis product in said cracking system to form a cracking product, or "cracked mix" comprising MAM and the acidic raw material; (v) continuously feeding at least a portion of said cracking product and methanol to an esterification reactor; and (vi) continuously reacting said portion of said cracking product and said methanol in the esterification reactor to form MMA. The acidic raw material serves as both a reactant and a solvent for the reaction. Preferred examples of the acidic raw material include sulfuric acid, oleum, and mixtures thereof. Using sulfuric acid at a concentration of greater than 95% is preferred, and a concentration of greater than 98% is more preferred. The hydrolysis system may contain a single reactor or multiple reactors connected in series and may also employ one or more reactant addition points.

From the esterification reactor, a liquid product mixture is fed to a first phase separator, e.g., a decanter, where a two-phase liquid separation occurs. The heavy, or denser, phase is an aqueous solution comprising practically all of the sulfuric acid as well as ammonium bisulfate, most of the water and methanol and lesser amounts of the other organic components. The lighter phase comprises most of the MMA product, and lesser amounts of water, by-product methacrylic acid, methanol, MAM and other organic components. The presence of sulfuric acid makes this phase separation quick and efficient due to the marked density difference between the two phases. The organic phase is drawn off and sent to a purification section for further separation of the product, as by distillation.

The process of the invention improves the ACH process by reducing the amount of fouling. Fouling reduction is accomplished by reducing the amount of polymer in the process equipment.

The esterification reactor, in which the methyl methacrylate is produced, also produces by-product methacrylic acid. The methacrylic acid is recovered and recycled to the esterification reactor via a neutralization system, in which the methacrylic acid-containing organic phase is contacted with a base, such as ammonia, ammonium hydroxide, sodium hydroxide or any other suitable base, and the methacrylic acid is converted to a water-soluble salt, e.g., ammonium methacrylate. The resulting mixture is sent to a second phase separator, e.g., a decanter, in which organic and aqueous phases are separated, and at least a portion of the ammonium methacrylate salt-containing aqueous phase is removed and indirectly recycled to the esterification reactor.

Over time, polymerized monomer accumulates in the interfacial region of the second phase separator. It starts out as lower molecular weight, soluble polymer. However, upon contact with the base, e.g., ammonium hydroxide, the polymer tends to act like a surfactant, e.g., contains both hydrophobic and hydrophilic functionality, with limited solubility in both the aqueous and organic phases. The functionalized polymer accumulates in the process at the organic/aqueous interface in the second phase separator, degrading the quality of the separation of the two liquid phases. This interfacial layer of functionalized polymer solids will be referred to as a "rag layer." Without intervention, the aqueous phase, which is recycled to the esterification reactor, eventually will contain soluble and entrained functionalized polymer, which further increases the amount of polymer formation in the reactor, thereby exacerbating the deposition of solids in process equipment.

In the process of the invention, a continuous or intermittent purge stream, or slip stream, is taken from the second phase separator. In one embodiment of the invention, the removal is accomplished by taking material primarily from the interfacial layer. However, it is also possible to remove some of the aqueous and/or organic layers, if desired. It is preferred to remove material from the second phase separator at the interface layer or just below the interface layer. In one embodiment of the invention, a slip stream is taken from the top of the aqueous layer, i.e., from a location that is immediately below the interface layer. Advantageously, the removal is accomplished from the side of the phase separation vessel. The exact piping arrangement is not critical, and can be configured in any suitable manner desired by one skilled in the art. In one embodiment of the invention, the removal significantly reduces the height, or thickness, of the rag layer, thereby enhancing phase separation performance. The process of the invention may lead to the eventual removal or substantial removal of the rag layer. One result of the process is that less polymer is recycled to the reactor, resulting in reduced polymer formation in the reactor. The destination and treatment or disposal of the purged rag material is not particularly critical, but preferably it is removed from the process. It preferably is not recycled to the reactor. The interfacial layer can be located via any suitable means, many of which are known to those skilled in the art. For example, the layer can be located by manual sampling, or can be located using instrumentation. Examples of instrumentation include instruments that rely on physical property differences between the upper and lower layer, such as electrical conductivity or density.

The invention will be explained in more detail by reference to certain preferred embodiments and with reference to the drawings. Referring now to the Figure, aqueous recycle feed 12 comprising water, methanol, ammonium methacrylate, and methyl methacrylate from recycle feed tank 105 is fed to heater 106. The effluent from heater 106 is withdrawn via line 11 and fed to mixing tee 100. A 'cracked mix' comprising MAM, sulfuric acid, water and cracking by-products is fed via line 10 to the other inlet of tee 100. The effluent from tee 100 is sent via line 14 to esterification reaction zone 101. The esterification reaction zone effluent, or first stream, 15 comprises MMA, water, MAA, methanol, ammonium bisulfate and sulfuric acid, and is sent to phase separator, or decanter, 102 where it phase separates into first organic liquid product phase, which is a primarily organic crude MMA phase comprising MMA, methanol and MAA, and first aqueous phase, which is a primarily aqueous phase comprising the acidic raw material, ammonium bisulfate and other components. The first aqueous phase from phase separator 102 is sent via line 16 to a separation or purification zone. The first organic liquid product phase is sent via line 17 to neutralization zone 103 where it is contacted with ammonia introduced via line 18 to produce a neutralized organic phase, comprising MMA, methanol and ammonium methacrylate. Neutralized stream 19, comprising the neutralized organic phase, is sent to a second phase separation zone 104. Additional water is fed to separation zone 104 via line 20 to improve the phase separation. In the second phase separation zone, an organic layer and an aqueous layer form. Stream 21, which comprises primarily MMA and is the organic layer from the second phase separator 104, is withdrawn from the second phase separation zone 104 and is sent for further purification. Stream 22, designated the second aqueous stream, comprises methanol and aqueous ammonium methacrylate and is taken from the aqueous phase of zone 104, and sent to recycle tank 105, where it optionally is mixed with at least one other aqueous recycle stream 23. Fresh methanol is fed to recycle tank 105 via line 24. From second phase separation zone 104, a slip stream or purge stream comprising soluble and/or insoluble polymer is withdrawn via line 13 and fed to stripping zone 107 where low boiling components such as water, MMA, and methanol are recovered and fed to recycle tank 105, via line 23.

The size of the purge stream can be tailored as needed to accomplish the degree of polymer reduction desired. For example, in the context of FIG. 1, the relative size of the purge stream can be described as a percentage of the total mass flow rate of the second aqueous stream. Thus, as an example for a continuous purge stream, the relative size of the purge stream is expressed as the size of stream 13 in lb./hr. divided by the size of stream 22 in lb./hr. In various embodiments of the invention, the relative size of the purge stream ranges from 0.1 to 7%, or from 0.5 to 4%, or from 1 to 2% of the total size of the second aqueous stream. Thus, if the flow rate of stream 13 is 5,000 lb/hr. and the flow rate of stream 22 is 100,000 lb./hr., then the relative size of the purge stream is 5,000/100,000×100=5%.

The process of the invention can be operated in a manner such that the concentration of soluble polymer in the second aqueous stream is controlled at a desired level. In various embodiments of the invention, the average concentration of soluble polymer in the second aqueous stream is less than 500 ppm, less than 400 ppm, less than 250 ppm, or less than 100 ppm, based on the weight of the second aqueous stream. Advantageously, the average concentration of soluble polymer in the second aqueous stream is from 1 to 500 ppm, from 2 to 400 ppm, from 5 to 250 ppm, or from 10 to 100 ppm.

A polymerization inhibitor can be employed in the process when the product and/or reactants comprise one or more polymerizable compounds. A wide variety of inhibitors are known and commercially available. The inhibitor may be added to the hydrolysis reactor alone or may be combined with another inhibitor and/or with a suitable solvent and then added to the process. Preferred solvents include, but are not limited to, acetone, ACH, trifluoroacetic acid, nitromethane, and/or sulfuric acid. Preferred solvents for use with phenothiazine inhibitors include one or more sulfur compounds. Such sulfur compounds include, but are not limited to, sulfuric acid, sulfur dioxide, methyl sulfone, tetramethylene sulfone ("sulfolane"), and dimethyl sulfoxide.

In various embodiments, the process of the invention may effectively reduce the concentration of polymer in the aqueous phase of the second phase separator by at least 60%, or at least 70%, or at least 85%, compared to a process that is identical except that it does not have the purge stream.

SPECIFIC EMBODIMENTS OF THE INVENTION

The following examples are given to illustrate the invention and should not be construed as limiting its scope.

EXAMPLE 1

A decanter, situated as the second phase separation zone 104 in the Figure, is fed a neutralized organic phase, comprising 58 wt % MMA, 5.6 wt % methanol, 16 wt % water, 17 wt % ammonium methacrylate, and 3.4% other primarily organic materials. The decanter is equipped with 5 nozzles that are vertically aligned on the side of the decanter. Each nozzle is valved and can be used to withdraw liquid from a different level in the decanter. The nozzles are numbered 1 to 5 in order from top to bottom. In this example, nozzle 5 is at a level that is below the interface layer in the decanter. A purge stream or slip stream of material is continuously withdrawn from nozzle 5 over a period of 22 days according to the schedule shown in Table 1.

Samples of the aqueous phase from the decanter, stream 22 in the Figure, are collected, and analyzed for soluble polymer via gel permeation chromatography (GPC). The results are shown in Table 1.

TABLE 1

| Results of Example 1 | | |
|---|---|---|
| Time from start of Purge | Rag Purge Flow Rate | Soluble Polymer |
| 0 days | 0 | 595 ppm |
| 3 days | 690 lb/hr | 945 ppm |
| 9 days | 689 lb/hr | 31 ppm |
| 22 days | 0 | 47 ppm |
| 30 days | 0 | 103 ppm |
| 35 days | 0 | 219 ppm |

Withdrawal of the slip stream has a dramatic effect on soluble polymer in the aqueous layer. As can be seen from Table 1, withdrawal of the slip stream of material from nozzle 5 reduces the amount of soluble polymer in the decanter.

EXAMPLE 2

The procedure of Example 1 is repeated for 21 days, except that the flow rate of the slip stream is varied.

The slip stream is operated over four distinct flow regimes. Frequent sampling of the aqueous layer is conducted for each flow regime. The flow rate and soluble polymer concentration are shown below in Error! Reference source not found.

TABLE 2

| Results of Ex. 2 | | |
|---|---|---|
| Time from start of Purge | Rag Purge Flow Rate | Soluble Polymer |
| 0 days | 0 | 828 ppm |
| 2 days | 767 lb/hr | 566 ppm |
| 5 days | 1,090 lb/hr | 201 ppm |
| 6 days | 997 lb/hr | 182 ppm |
| 7 days | 1,507 lb/hr | 89 ppm |
| 10 days | 1,958 lb/hr | 101 ppm |
| 12 days | 1,354 lb/hr | 40 ppm |
| 13 days | 1,096 lb/hr | 145 ppm |
| 14 days | 586 lb/hr | 175 ppm |
| 17 days | 489 lb/hr | 207 ppm |
| 24 days | 0 | 160 ppm |
| 25 days | 0 | 544 ppm |
| 26 days | 0 | 575 ppm |
| 27 days | 0 | 319 ppm |
| 45 | 0 | 1,517 ppm |

The response in soluble polymer concentration is similar to that observed in Example 1. Over the first 7 days with a purge rate of about 1,000 lb/hr, the lower layer soluble polymer concentration drops from 566 ppm to 89 ppm. For days 8-11, the rag purge flow rate is increased to ca. 2,000 lb/hr. Soluble polymer levels decrease again from 89 ppm to 40 ppm. For days 13-17, the rag purge flow rate is reduced to ca. 500 lb/hr. Soluble polymer levels rise, but to levels similar to those of the initial period, i.e., in the 200 ppm range. The rag purge flow rate is then set to zero for the remainder of the experiment, and the level of soluble polymer increases. Further sampling is conducted in subsequent weeks, and the level of soluble polymer is in the range of about 1,000-1,500 ppm. Thus, the beneficial effects of the rag purge are lost when the purge is stopped.

A summary of soluble polymer reduction achieved in Ex. 2 is shown in Table 33 below.

TABLE 3

Ex. 2 Soluble Polymer Reduction Summary

| Flow Rate (lb/hr.) | Lowest Soluble Polymer (ppm) | % Reduction |
|---|---|---|
| 0 | 828 | — |
| ca. 1,000 | 89 | 89% |
| ca. 2,000 | 40 | 95% |
| ca. 500 | 208 | 75% |

EXAMPLE 3

An esterification reaction is conducted at 138° C. and 80 psig under a nitrogen atmosphere by feeding to a reactor 267.4 g/hr. of a cracked mix feed stream comprising 154.4 g of sulfuric acid, 94 g of methacrylamide, 2.7 g water and 16.3 g cracking by-products generated by cracking HIBAM and SIBAM. A second feed stream comprising 231 grams/hr. of a recycle feed comprising 45% water, 35% methanol, 5% MMA, and 15% ammonium methacrylate is also fed to the reactor. During the reaction time, the pressure and temperature in the reactor are maintained at 80 psig and 138° C. The contents of the reactor are cooled and forwarded to a decanter, where two liquid phases, organic and aqueous, separate. The organic phase is sampled and analyzed for soluble polymer. The aqueous phase is recycled to the reactor as part of the second feed stream. A sample of the second feed stream is also analyzed for soluble polymer.

Polymer levels are shown in Table 4 below. The data is split into two categories: (1) experiments using recycle feed collected when a slip stream is being purged from the decanter and (2) experiments using recycle feed collected without a purge from the decanter.

TABLE 4

Comparison of Baseline Laboratory Soluble Polymer Outside/During Rag Purge Operation

| | Recycle Feed Soluble Polymer | Reactor Effluent Organic Layer Soluble Polymer |
|---|---|---|
| Without Purge Stream | 92 ppm | 1,794 ppm |
| With Purge Stream | 88 ppm | 393 ppm |

The data show that operating the process with the polymer-removing purge stream or slip stream results in surprisingly lower polymer concentrations in the esterification reactor effluent. One conclusion from this is that less polymer is produced in the esterification reactor when the purge stream is operating.

What is claimed is:

1. A process for producing methyl methacrylate (MMA) comprising: (a) contacting methacrylamide (MAM) with methanol in an aqueous reaction medium in an esterification reaction zone in the presence of an acidic raw material selected from the group consisting of sulfuric acid, oleum, and mixtures thereof, to produce a first stream comprising MMA, water, methanol, acidic raw material and methacrylic acid (MAA); (b) phase separating the first stream in a first phase separating apparatus into a first aqueous phase comprising the acidic raw material, and a first organic liquid product phase comprising: MMA, methanol and MAA; (c) taking a first organic stream from the first organic liquid product phase, and neutralizing the MAA of the first organic stream with ammonia to produce a neutralized stream comprising MMA, methanol and ammonium methacrylate; (d) optionally adding water to the neutralized stream; (e) phase separating the neutralized stream in a second phase separating apparatus into an organic layer comprising MMA and an aqueous layer comprising methanol and ammonium methacrylate, the layers having a common interface; (f) removing a polymer-removing stream from the phase separating apparatus at or below the height of the interface; and (g) removing from the second phase separating apparatus a second aqueous stream comprising a portion of the aqueous layer and from 1 to 500 ppm of a soluble polymer and wherein the second aqueous stream is recycled to the esterification reaction zone wherein the polymer-removing stream has a relative size compared to the second aqueous stream, and the relative size is from 0.1 to 7% of the size of the second aqueous stream.

2. The process of claim 1 wherein water is added to the neutralized stream.

3. The process of claim 1 wherein the relative size of the polymer-removing stream is from 0.5 to 4%, of the size of the second aqueous stream.

4. The process of claim 1 wherein the relative size of the polymer-removing stream is from 1 to 2%, of the size of the second aqueous stream.

5. The process of claim 1 wherein the concentration of soluble polymer in the second aqueous stream is less than 400, less than 250 ppm, or less than 100 ppm, based on the weight of the second aqueous stream.

6. The process of claim 1 wherein the concentration of soluble polymer in the second aqueous stream is from 2 to 400 ppm, from 5 to 250 ppm, or from 10 to 100 ppm, based on the weight of the second aqueous stream.

* * * * *